US007337777B1

(12) United States Patent
Islava

(10) Patent No.: US 7,337,777 B1
(45) Date of Patent: Mar. 4, 2008

(54) AIRWAY STABILIZER FOR RESUSCITATION

(76) Inventor: Steven Islava, 17336 Bonaire Way, Newport Beach, CA (US) 92660

( * ) Notice: Subject to any disclaimer, the term of this patent is extended or adjusted under 35 U.S.C. 154(b) by 0 days.

(21) Appl. No.: 11/092,393

(22) Filed: Mar. 29, 2005

(51) Int. Cl.
*A61F 13/00* (2006.01)
*A61B 19/00* (2006.01)

(52) U.S. Cl. .................. 128/202.28; 128/845; 128/846

(58) Field of Classification Search ................ 128/845, 128/846, 865, 870, 202.28, 202.24, 203.11; 5/631, 632, 652, 636; 2/10, 468; 441/88; 602/13, 18
See application file for complete search history.

(56) References Cited

U.S. PATENT DOCUMENTS 3,461,858 A * 8/1969 Irving .......................... 601/41
3,988,499 A * 10/1976 Reynolds .................... 428/216
4,124,757 A * 11/1978 Hoffer ........................ 128/846
4,297,999 A * 11/1981 Kitrell ................... 128/205.16
4,805,603 A * 2/1989 Cumberland ................. 602/13
4,918,774 A * 4/1990 Popitz ........................... 5/644
5,494,048 A * 2/1996 Carden .......................... 5/622
D368,524 S 4/1996 Reedus
5,569,176 A 10/1996 Graham
5,634,222 A * 6/1997 Zwickey ........................ 5/628
5,682,632 A * 11/1997 Cotroneo ....................... 5/636
5,713,841 A * 2/1998 Graham ....................... 602/32
5,898,963 A * 5/1999 Larson .......................... 5/644
5,916,185 A 6/1999 Chitwood
6,116,781 A * 9/2000 Skeens ....................... 383/100
6,327,725 B1 12/2001 Veilleux
6,331,170 B1 12/2001 Ordway
6,622,857 B2 * 9/2003 Ohtsubo et al. ............ 206/287
6,814,491 B1 * 11/2004 Tang .......................... 383/100
7,047,976 B2 * 5/2006 Frank ......................... 128/846
7,077,141 B2 * 7/2006 Troop ......................... 128/845
2003/0151295 A1 * 8/2003 Nelson .................. 297/452.17
2004/0049228 A1 * 3/2004 Lope .......................... 606/240

* cited by examiner

*Primary Examiner*—Teena Mitchell
(74) *Attorney, Agent, or Firm*—Myers Dawes Andras & Sherman LLP

(57) ABSTRACT

A simple and compact device permits a single rescuer to quickly place a prone patient's airway in an optimal, open configuration. The device consists of a reversibly collapsed neck support that can rapidly be placed underneath the neck of an unconscious patient lying prone on his back. The collapsed support can be inflated to returned it to a not collapsed state for elevating a portion of the patient's neck. The support is shaped to come to an apex so that the pressure is applied to a restricted region of the neck. When gentle elevating pressure is applied to a small region of the neck, the neck "fulcrums" with the head remaining in contact with the ground and the free portion of the neck being elevated. This results in the optimum extension to open the airway without having to pull on the patient's jaw. Once the airway is open, it is relatively simple to place a tight fitting resuscitation mask over the patient's mouth.

13 Claims, 14 Drawing Sheets

10
24
42
38
36
40
34

AIRWAY STABILIZER FOR RESUSCITATION

BACKGROUND

1. Area of the Art

The present invention is in the art of emergency medical equipment and is more specifically directed to a device for ensuring an open airway and positioning for intubation during resuscitation of an unconscious patient.

2. Description of the Background

As a result of a variety of different accidents and medical emergencies an unconscious individual will cease breathing. It is essential to quickly restore breathing so that oxygen deficit does not result in brain damage or other organ damage. Generally, oxygenation and breathing can be restored by forcing air or oxygen into the individual's lungs. Air or oxygen will then naturally exit if the forcing pressure is temporarily discontinued. By continually repeating the process ventilation of the lungs can be maintained until the individual can takeover and begin to breath naturally. Air can be forced into the lungs by means of mouth to mouth resuscitation or by means of a mask that forces air or oxygen into the unconscious patient's mouth.

Loss of consciousness or any condition that leads to lack of tone or unresponsiveness of the muscles of the jaw or tongue can cause the tongue or the epiglottis to fall towards the back of the throat thereby obstructing the airway. This is commonly known as "swallowing one's tongue." To deal with such a situation a rescuer needs to open the airway by tilting the patient's head back and lifting the chin (i.e., hyperextending the patient's neck which involves a maneuver where the jaw of a prone, unconscious patient is pulled gently forward while the individual's head is tipped slightly backwards). This pulls the tongue away from the trachea and opens the airway. If the patient starts spontaneously breathing on their own, the rescuer imply needs to continue to hold the airway open (i.e., maintain the correct neck position). If, however, the patient does not spontaneously breath, it will be necessary to hold the airway open while the patient is artificially ventilated. This requires one to place a resuscitation mask with attached resuscitator can be placed over the patient's nose and mouth. The resuscitator bag is then squeezed to force air into the patient's lungs.

All too frequently, the airway will not be optimally opened. This may result in failure to adequately ventilate the lungs. Instead of directing air to the lungs the air may find its way into the patient's stomach. This can lead to more than bloating of the patient; it may provoke vomiting with the significant danger that the vomitus will be inhaled by the patient. Such inhalation can lead to serious later medical consequences assuming that it does not altogether prevent resuscitation.

If it is not possible to adequately open the airway, the solution may be to intubate the patient. The patient must be placed in the correct hyperextended position neck to perform endotracheal intubation. Intubation is performed by inserting an "L" shaped device with a light at the tip to lift the jaw and tongue so as to visualize the patient's vocal cords. At that point an endotracheal tube can be inserted through the vocal cords and into the lungs. Once the tube has been inserted approximately two inches past the vocal cords, it is essential to stabilize the tube by taping it to an endotraceal tube holder. Then the rescuer can ventilate the patient through the tube and does not to hyperextend the neck and get a good seal with a mask. When the endotracheal tube is in place it is important to stabilize the patient's head position lest movement cause the tube to be pulled out.

Inflatable bladders have been used in a variety of medical and non-medical contexts for providing support and comfort. For example U.S. Pat. No. Des. 368,524 to Reedus shows a design for an inflatable lumbar design pillow. U.S. Pat. No. 6,331,170 to Ordway discloses an adjustable back support belt including an inflatable portion. U.S. Pat. No. 6,327,725 to Veilleux et al. discloses an inflatable pillow that includes neck support. U.S. Pat. No. 5,916,185 to Chitwood discloses a cervical traction and stretching device that includes an inflatable portion. U.S. Pat. No. 5,569,176 to Graham discloses a cervical traction and exercise device that includes an inflatable elongated bladder for placing pressure upon a user's neck.

However, none of the prior art devices are structured or intended to provide forces to ensure opening of an unconscious patient's airway.

SUMMARY OF THE INVENTION

The present invention is a simple and compact device that permits a single rescuer to quickly place a prone patient's airway in an optimal, open configuration. The device consists of a reversibly collapsible neck pad or support that can rapidly be placed beneath the base of the neck of an unconscious patient lying prone on his back. Because the device is quite compact when uninflated or collapsed, it can be readily slid under the patient's shoulders and lower neck.

The device consists of a neck support for elevating a portion of the patient's neck. The support can consist of a collapsed inflatable bladder or a collapsible foam or even a foldable support. In the bladder embodiment the bladder is shaped to form a contacting region so that the pressure is applied at a relatively short region of the neck near the point the neck joins the shoulders. The collapsible and foldable versions similarly apply pressure to a short region of the neck. When gentle elevating pressure is applied to this region of the neck, the rest of the neck "fulcrums" (that is, the contacting region of the support acts as a fulcrum) with the head remaining in contact with the ground (or the remaining portion of the inventive device) and the free portion of the neck bring slightly elevated. This results in the optimum extension to open the airway without having to pull on the patient's jaw. Once the airway is open, it is relatively simple to place a tight fitting resuscitation mask over the patient's nose and mouth. The device can also be equipped with inflatable or collapsible "wings" to support either side of a patient's head and to act as attachment for straps to stabilize the head and to hold the resuscitation mask.

While the bladder or other support can directly provide a point of elevation to act as a "fulcrum" for the neck, it is also possible to provide the support with a terminal pad shaped to contact the neck and provide force over an optimum length of the neck. The support (and any attached or integral pad) normally provides up to about four inches of elevation although taller supports can be provided depending on patient size. In the inflatable embodiment the bladder is attached to an inflation device such as a pneumatic bulb like those found on blood pressure cuffs. The bladder can be fully inflated within a few seconds. The rescuer can inflate the bladder with one hand while fitting the resuscitation mask with the other. It is simple to increase or decrease the degree of bladder inflation if necessary to achieve optimal opening of the airway. When the support is provided by a collapsible foam or foldable structure, the entire device can be moved in a direction parallel to the patient's spine to move the region of contact with the neck until the neck "fulcrums" to open the airway.

DETAILED DESCRIPTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an airway stabilizing device for opening the airway of an unconscious patient.

Figure 1:
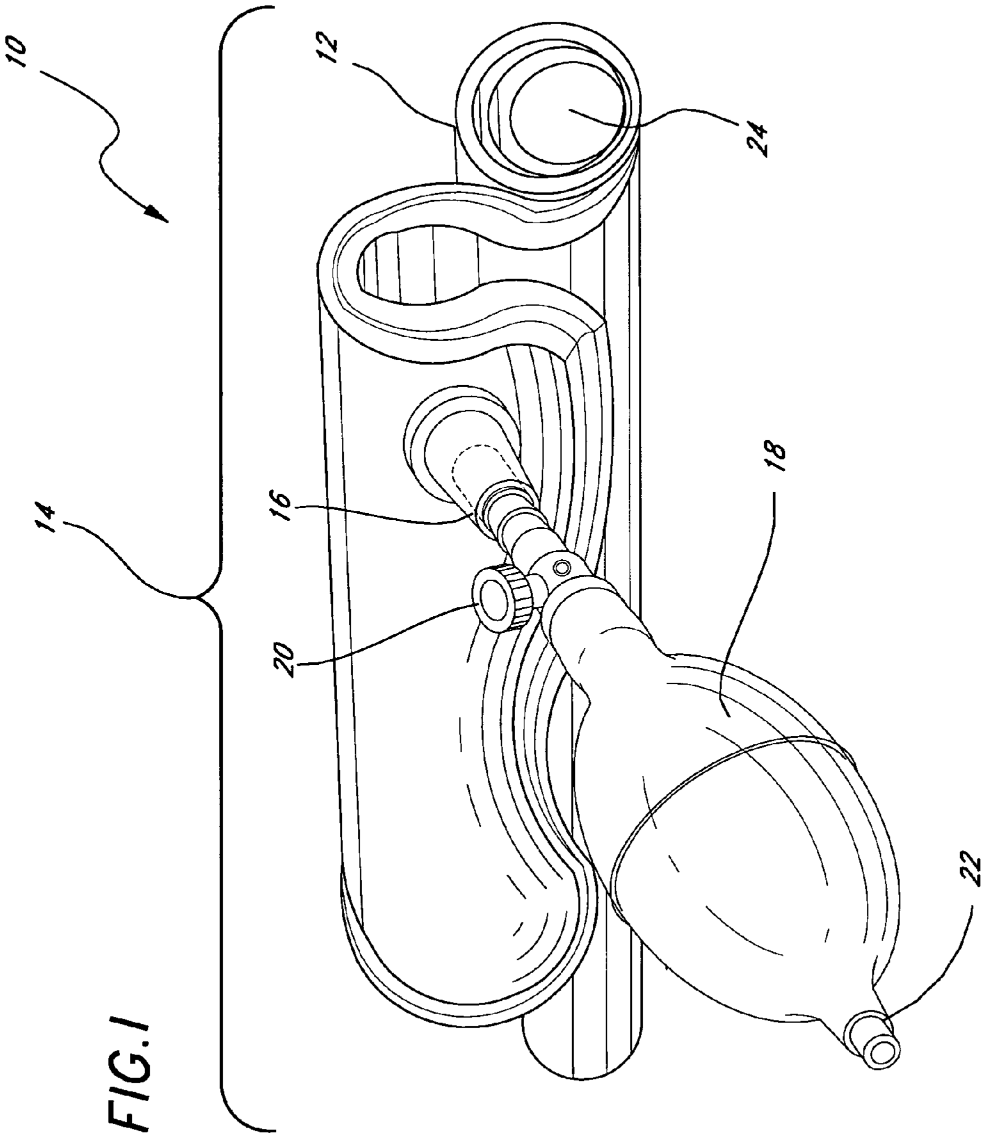
FIG. 1 is a drawing of one embodiment in a collapsed state.

FIG. 1 shows a view of the inflatable bladder embodiment of the neck support device 10 in a collapsed state. A collapsed, inflatable bladder 12 made of relatively thin polyethylene or vinyl or other suitable plastic takes up little space. For simplicity, the bladder 12 is shown having a single compartment, but the bladder may also have a more complex structure composed of multiple inflatable compartments. A hose 16 is in fluidic communication with an inflation source 18, here a rubber or plastic inflation bulb 18 equipped with a one way refill valve 22, and attaches the bladder 12 to the inflation device 18. A valve 20 is provided to control inflation and deflation of the bladder 12. It will be appreciated that the length of the hose 16 is a matter of design. A compact unit can be made by having the inflation device 18 attached directly to the bladder 12 (that is, the hose 16 would be omitted or be extremely short). Alternatively, the hose 16 can be much longer so that a rescuer can pump up the bladder with one hand while stabilizing or otherwise working on the patient with the other hand. An advantage of the short hose configuration is that the entire device 10 can be so compact in its deflated or collapsed configuration so as to readily fit in a small package or pouch. It will also be appreciated that any other convenient inflation device can be used. Such devices include motorized pumps, sources of compressed gas such as a cylinder or aerosol can or cylinder-based pumps (such as the ubiquitous bicycle pump). The choice of inflation device is a matter of cost versus convenience. While a motorized pump is more expensive and may be heavier, it permits rapid inflation with essentially no effort on the part of the rescuer. The inflation device or the bladder 12 could be equipped with a regulating system such as a valve to adjust the degree of inflation. In the case of a motorized pump, the pump can simply have a reverse mode to pump gas out of instead of into the bladder 12. It should also be appreciated that the bladder 12 can be "self-inflating" by enclosing a structure of spaced apart springy or resilient fibers in a tangle or network. This structure has the shape and size of the inflated bladder; When the bladder is compressed or when air is drawn from the bladder by—for example—a vacuum pump, the structure collapses under atmospheric or compression weight. If a valve or some other similar device prevents reentry of air, the bladder remains compressed. When the air is allowed to return, the springy spaced apart material returns to its original shape, drawing air into the bladder as it presses outward on the bladder wall—thus "self-inflating" the bladder—with the atmosphere essentially behaving as the inflation device. This method is well-known and is commonly used to self-inflate air mattresses and the like.

Figure 2:
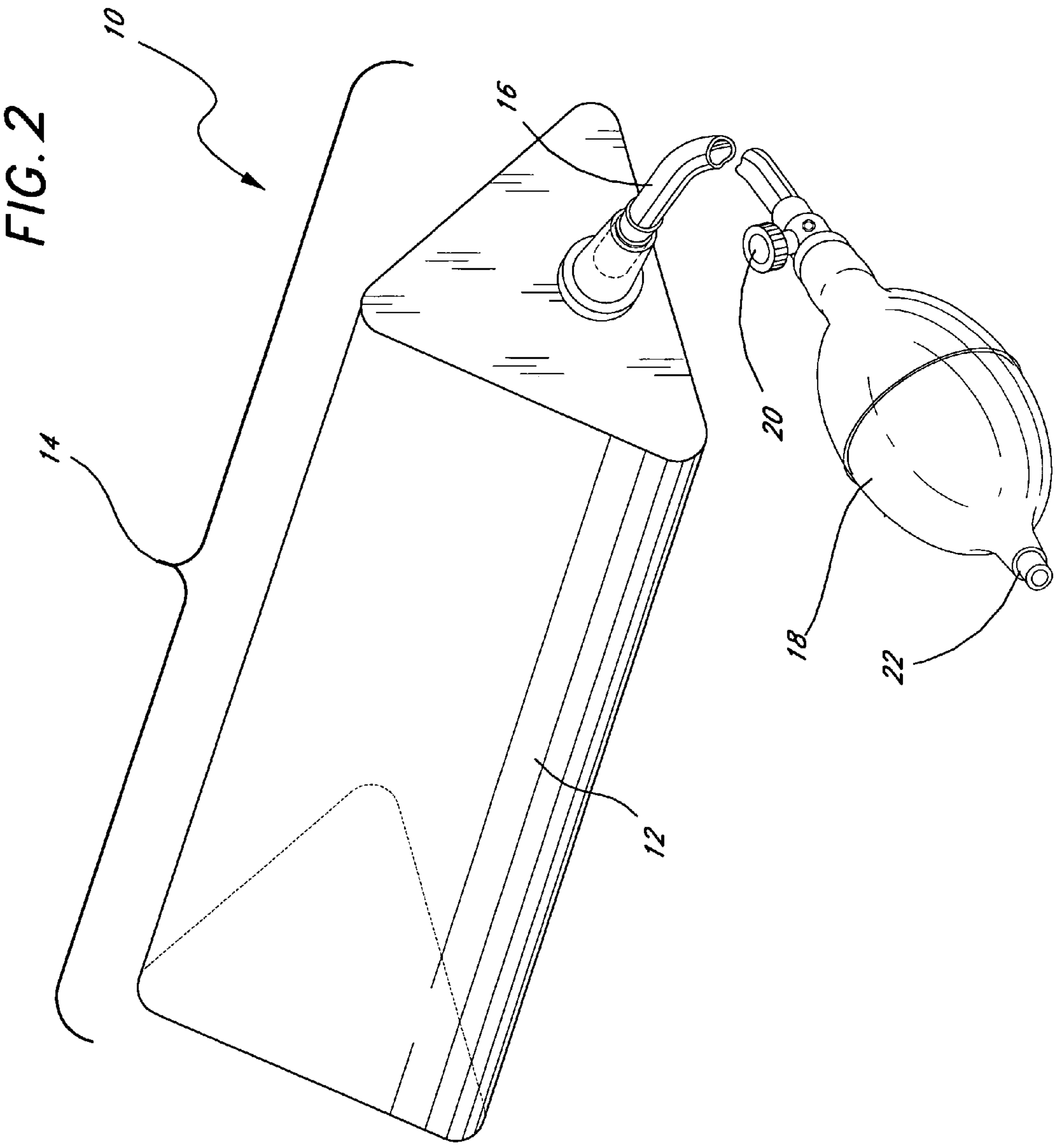
FIG. 2 is a perspective drawing of the embodiment of FIG. 1 in a fully inflated state.
Figure 3:
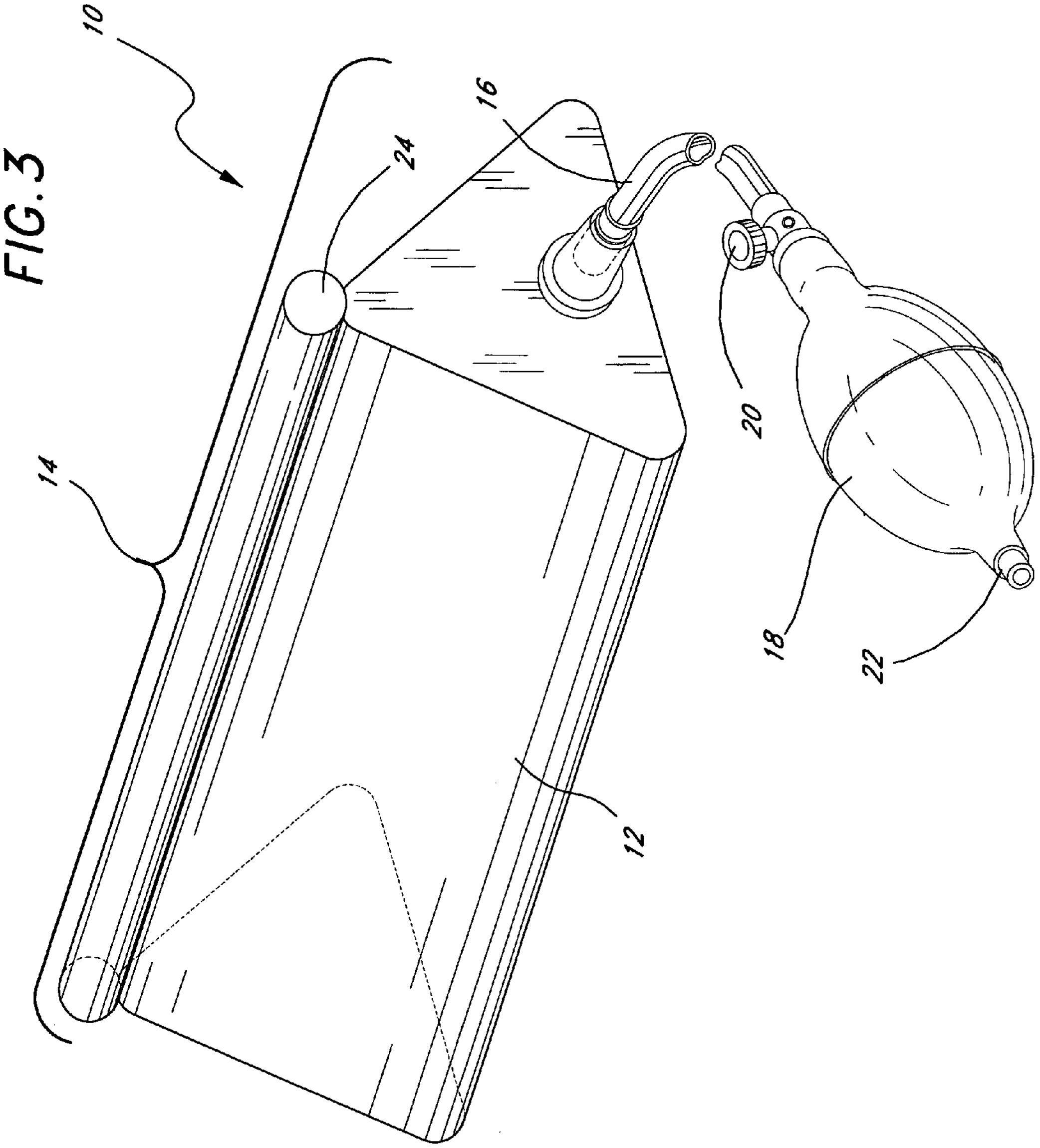
FIG. 3 is a perspective drawing of a second embodiment of the device in a fully inflated state.

FIG. 2 shows one embodiment of the device 10 in a fully inflated state with a bladder 12 that is essentially triangular in cross-section. The apex of the triangle provides a relatively narrow contact region 14. Other cross-sectional shapes are useable, but the dimension of the contact region 14 is of some importance. The contact region is intended to put pressure on a relatively specific length of a patient's neck vertebrae at or near the base of the neck to the scapula (vertebrae cervical 6 to thoracic 3). If the contact region 14 is too long (measured along the length of the patient's neck), the entire neck (or even upper back) could be lifted rather than bent ("fulcrummed") to open the airway. For example, a bladder trapezoidal in cross section will work where the contact region is not more than about 3 inches in length. Other bladder shapes that provide a contact region 14 with the within the proper dimensional range may be used. FIG. 3 shows a second embodiment where the contact region 14 is provided by a pad 24. Here the pad 24 is circular in cross-section and provides a contact region 14 of a relatively minimal length. Other pad configurations are functional provided the contact region 14 does not become too long.

The pad 24 can advantageously be constructed from plastic foam although other resilient material can be used as well. In the figure the pad 14 is integral to the unit and is permanently fused to the bladder 12. The pad may even be within the bladder. The foam of the pad 14 is sufficiently flexible that the deflated unit can readily be folded into a small package. However, it is also possible to make the pad 14 from a more rigid material that defies folding into a small package. The pad 14 can be designed to be easily removable. For example, it is possible to use ties, buttons, snaps, hooks zippers, hook in loop fastener (Velcro®) or other such devices to connect the pad removably to the bladder 12. With such system it is possible to use a rigid pad 14 or to use a disposable sterile pad 14 for each patient while the bladder 12 and the inflation device (bulb 18 and valve 20) can be used repeatedly for successive patients.

In use the device 10 is inserted beneath the base of the neck and shoulders of a prone patient (preferably on a "back board" so that the patient can later be transported without disturbing the patient's neck) so that when the bladder 12 is inflated optimally, pressure will be put on the vertebrae at the base of the neck and the patient's neck will pivot the exact amount to completely open the patient's airway. The rescuer can operate the inflation device while peering into the patient's mouth to judge when the bladder is optimally inflated. For example, when the patient's neck has optimally pivoted, the vocal cords should be visible at the back of the throat. If the inflation (i.e., the pivoting of the neck is too little or too great, it can be readily adjusted before placing a tight fitting resuscitation mask over the patient's nose and mouth. Adjustment can also be obtained by stabilizing the patient's head and moving the device 10 either towards the patient's head or towards the patient's shoulders so as to alter the precise region of the spine that is elevated. This will alter the degree of pivoting of the neck.

Figure 4:
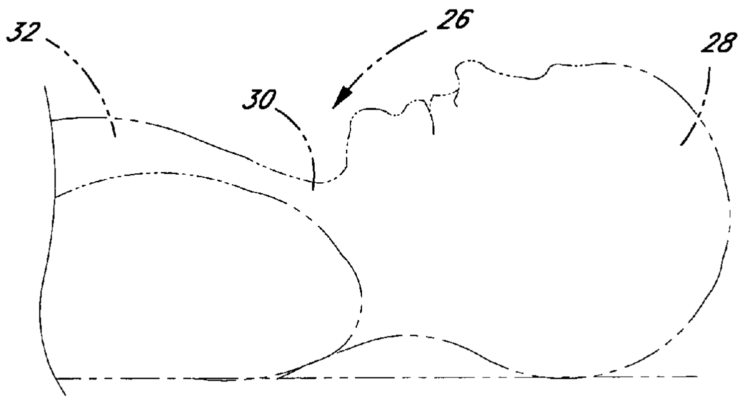
FIG. 4 is a view of an unconscious patient.
Figure 5:
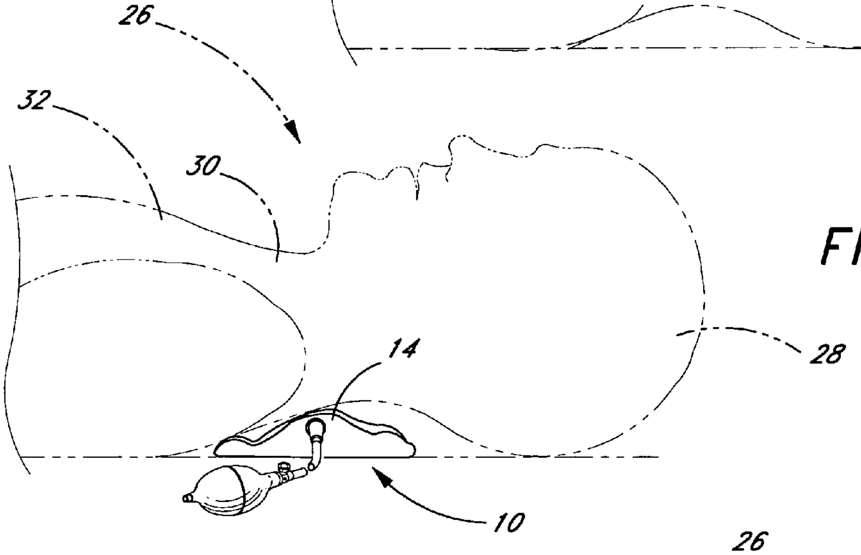
FIG. 5 is a view of the embodiment of FIG. 1 in a partially inflated state with an unconscious patient of FIG. 4.
Figure 6:
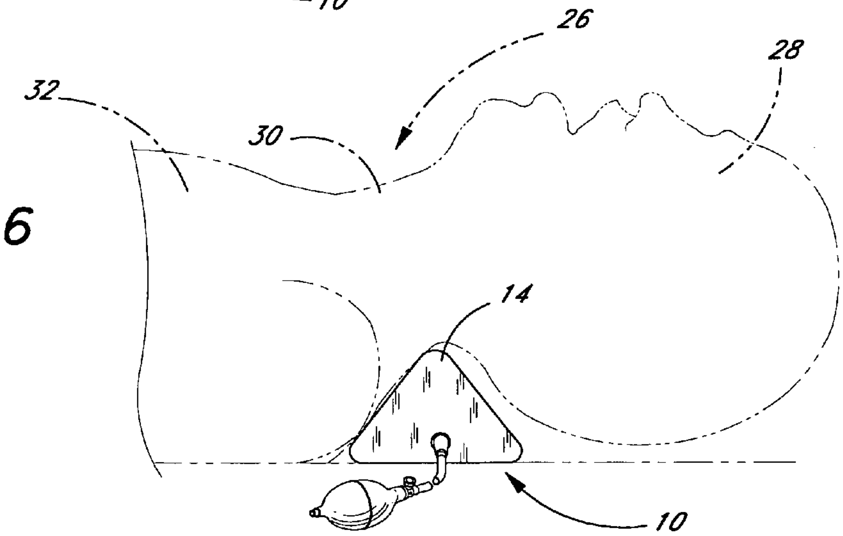
FIG. 6 is a view of the embodiment of FIG. 1 in a fully inflated state with the unconscious patient of FIG. 4.

The method of controlling neck pivoting by altering the degree of device inflation is demonstrated in FIG. 4 which shows a prone patient 26. FIG. 5 shows a side view of a collapsed device 10 slid under the shoulders/lower neck 30 of the patient 26. In FIG. 5 the device is partially inflated so that it is possible to see that the contact region 14 will contact the patient's vertebrae at the juncture between the neck 30 and the shoulders 32. As seen in FIG. 6 the fully inflated device 10 elevates the base of the neck so that the neck 30 fulcrums while the head 28 tilts so as to completely open the airway.

If it becomes necessary to intubate a patient, the visibility of the vocal cords can be checked and the inflation corrected so that the tube can be easily slid between the vocal cords and into the trachea (as opposed to entering the esophagus). Once the optimal elevation to open the airway is achieved, it is advantageous to stabilize the position of the device 10 and the patient's head 28 with a strap or straps 34.

Figures 7A, 7B:
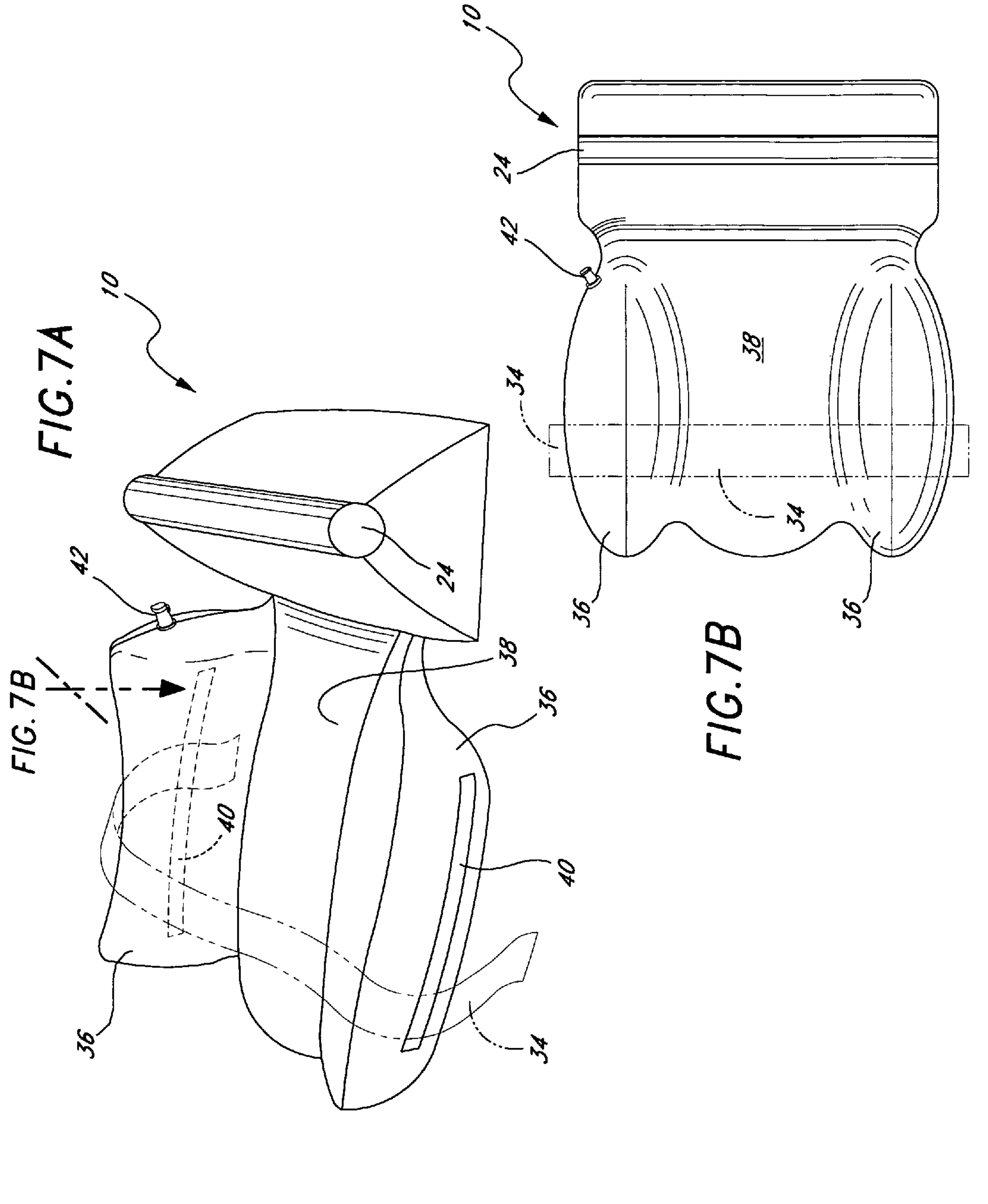
FIG. 7A is a view of a second embodiment of the device with inflated head support wings and straps to prevent motion of a patient.
FIG. 7B is a view of the embodiment of FIG. 7A showing the head support wings not fully inflated.
Figure 8:
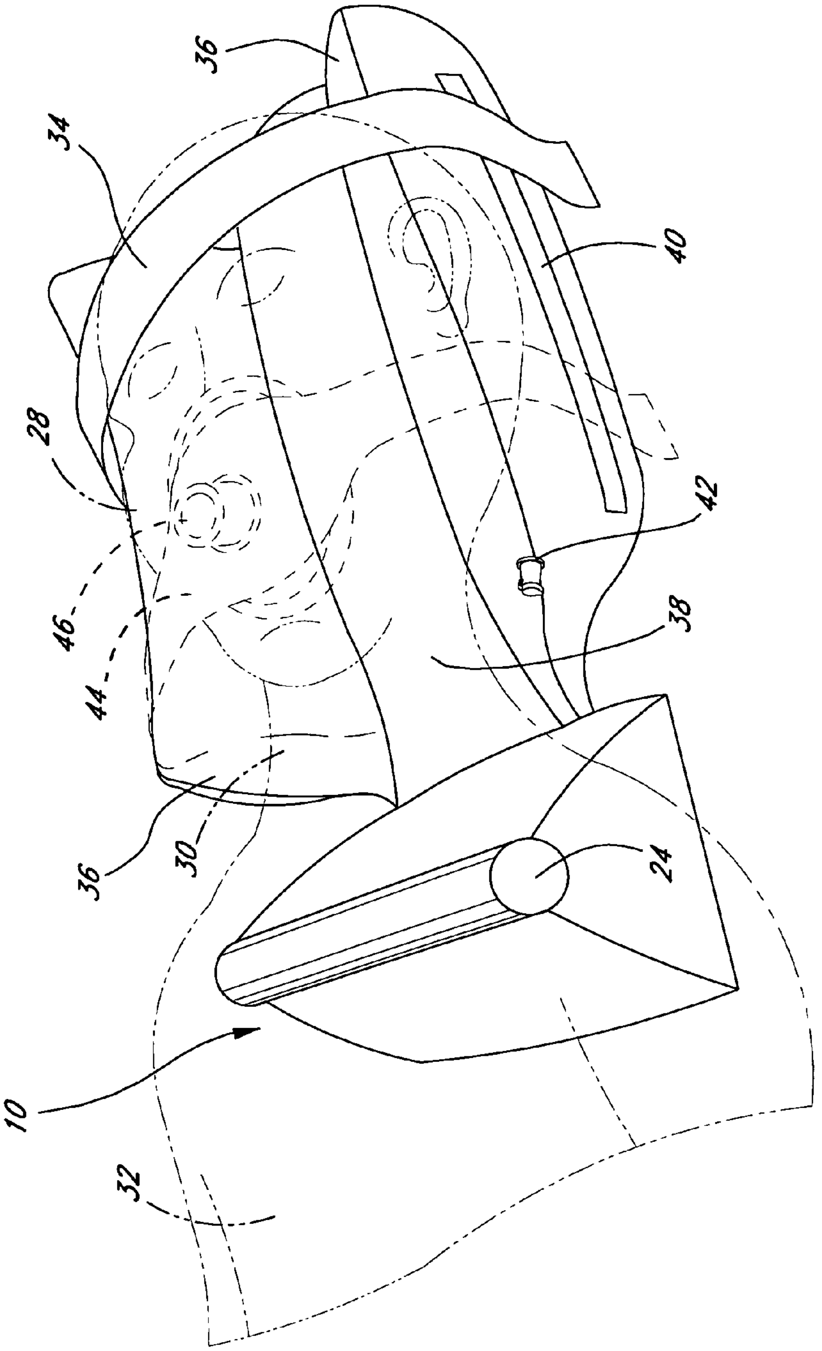
FIG. 8 is a view of the device of FIG. 7A shown in relationship to an unconscious patient (in phantom)

FIG. 7A shows a second embodiment of the device 10 intended to stabilize the head 28-neck 30 relationship with straps 34. In this embodiment head support wings 36 are attached to a basal connector 38 to which the bladder 12 is also attached. The head support wings 36 are intended to support either side of the patient's head 28 so that the head 28 is nestled between the wings 36 as shown in FIG. 8. As is also shown in FIG. 8 one strap 34 extends from one wing 36 to the other wing 36 across the patients forehead. A second optional strap 44 can be used to fix the position of the resuscitation mask 46 over the patient's mouth and nose. To attach the straps 34, 44 it is convenient to equip the straps 34, 44 and the wings 36 with hook in loop fastener (strip 40) although adhesives or other types of temporary fasteners can also be used. In this embodiment it is possible to use a repositionable fastening system (i.e., adhesive, hook in loop fastener and the like) to connect the device to the basal connector 38 so that the distance between the device 10 and the support wings 36 can be varied to control neck pivot. Alternatively, the bladder 12 and the support wings 36 can be permanently fixed together without use of a basal connector 38.

As shown in FIG. 7B, the head support wings 36 can advantageously be inflatable bladders not unlike the primary bladder 14 so that the entire device can be compactly stored. It is generally not important to be able to adjust the inflation of the wings 36; rather it is more important for them to be easily and rapidly inflatable. This can be achieved by injecting gas or air through an inflation port 42. The wings 36 can be inflated by mouth or an automatic inflation system relying on a cartridge of compressed gas or a chemical gas source (such as that used in an automobile air bag) or some other source of inflation gas. Of course, all such methods of inflation can also be used to inflate the bladder 12. The wings 38 can also be made "self-inflating" by enclosing a springy material inside the wings. When the inflation port 42 is opened, the springy material expands and draws air into the wings 36. The port 42 can then be closed so that the enclosed air will not escape. As explained above this same technique can also be used to "automatically" inflate the main neck support bladder 12. In that case the atmosphere acts as the "inflation source" as the bladder "sucks" in air. It is also possible to construct the wings 36 from plastic foam or similar material or even flat pieces of cardboard or the like which can be unfolded and interlocked to form the head support wings. In addition, the neck support device can be produced from foam or even assembled from a flat material like cardboard.

Figures 9A, 9B:
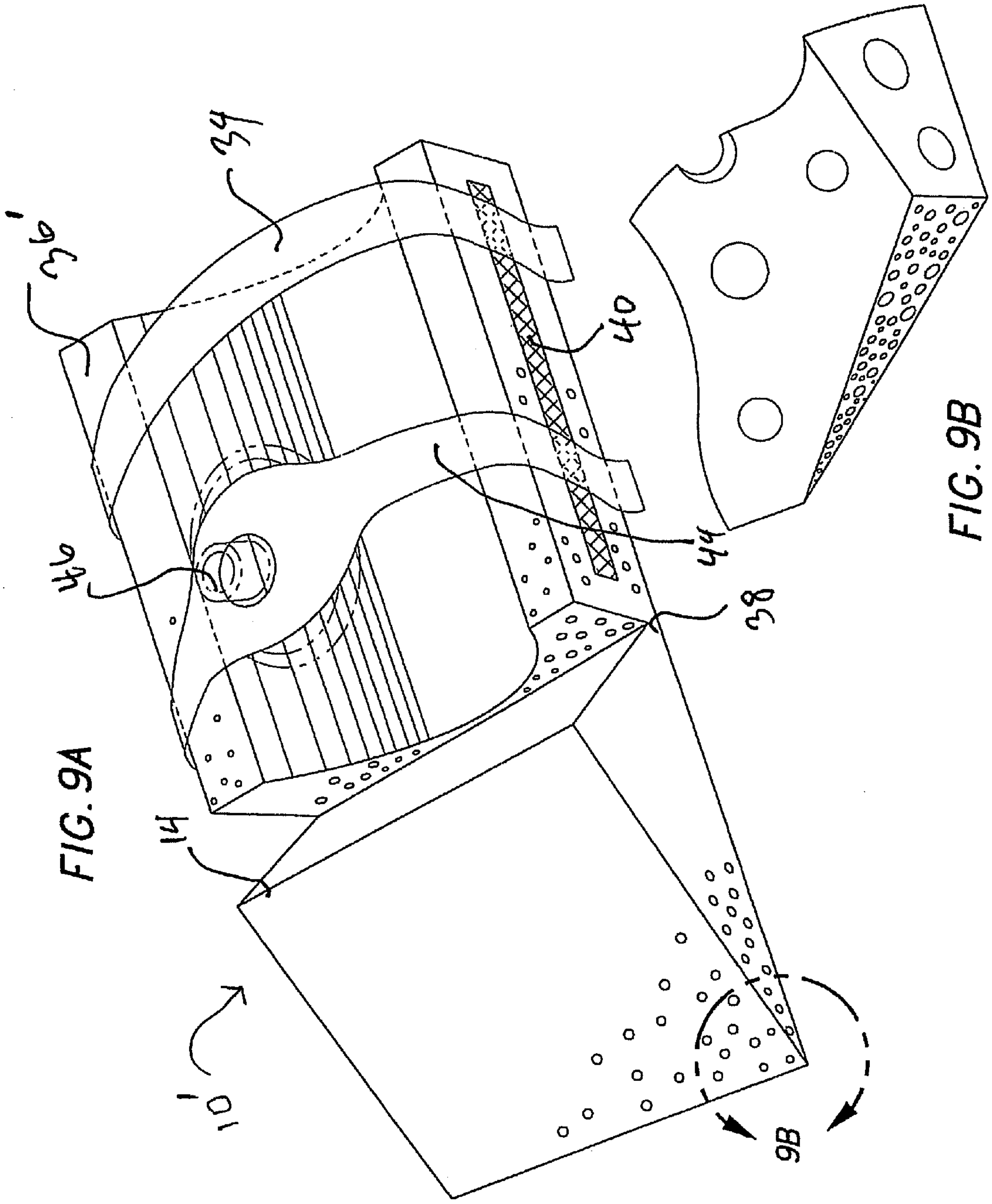
FIG. 9A shows an embodiment similar to the embodiment of FIG. 7A where the entire device is formed from open cell plastic foam.
FIG. 9B shows a magnified view of the foam of FIG. 9A.
Figure 10:
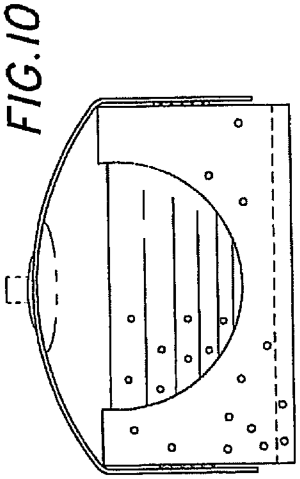
FIG. 10 shows the embodiment FIG. 9A as viewed from the open end of the head support region.
Figure 11:
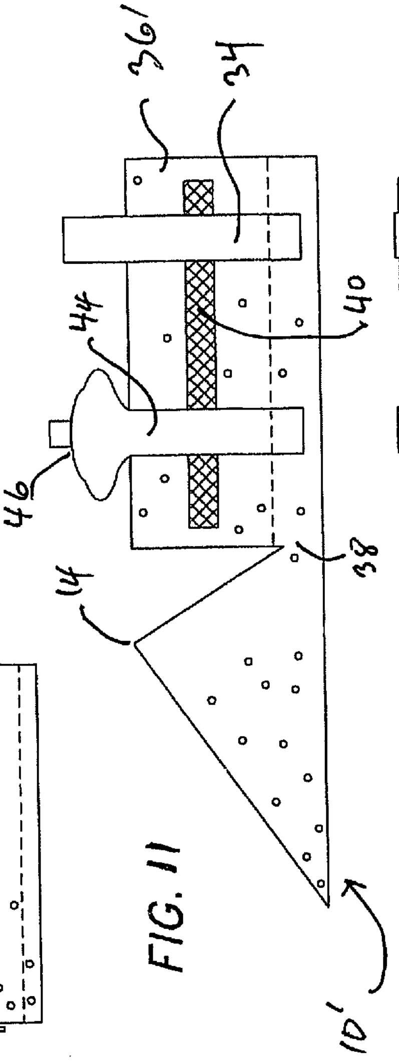
FIG. 11 shows the embodiment of FIG. 9A as viewed from the side.
Figure 12:
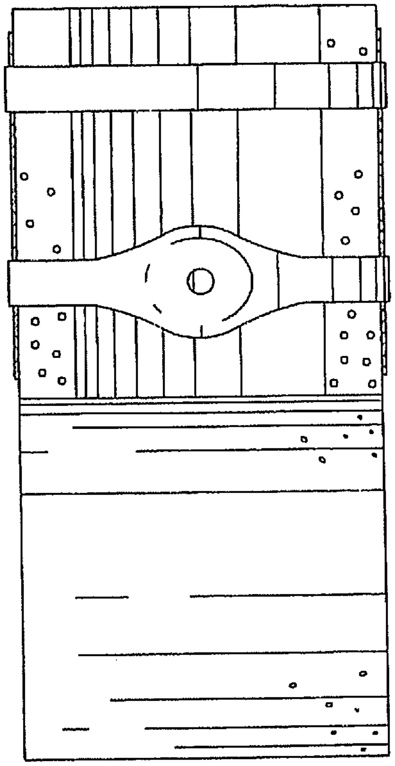
FIG. 12 shows the embodiment of FIG. 9A as viewed from above.

A potential disadvantage of a foam embodiment of the neck support and head support is that it is somewhat bulky for convenient storage. The inventor has avoided this disadvantage by perfecting a method of reversibly collapsing open cell plastic foam (urethane open cell foam and similar resilient open cell foams). When reversibly collapsed, the foam can act as a self-inflating member with the atmosphere acting as an inflation source. FIG. 9A shows a foam embodiment including both the head support wings 36' and the neck support device 10'. In this version the neck support 10' is formed from the same piece of foam as the head support wings 36'. These portions are joined by a connecting region 38'. FIGS. 10, 11 and 12 show the device of FIG. 9A viewed from different vantages so that the structure can be fully appreciated. Such a device can be produced by cutting or machining from a block of foam, or it can be assembled from several pieces of shaped foam. Alternatively, foam can be extruded into a mold to produce the device directly. It will be apparent to one of skill in the art that either the neck support 10' or the head support wings 36' alone could be made of foam with the other portion formed from alternative materials such as inflatable bladders or even foldable parts. When the two portions are separately formed, they can be hooked together by means of any of the usual fastening devices (such as hook in loop fasteners) either connecting the neck support directly to the head support wings or connecting each of these portions to a common backing such as a sheet of cardboard. An advantage of the common backing is that the positional relationship of the neck support relative to the head support wings can be adjusted so that the contact region 14 falls on an optimum region of the patient's neck.

Figure 14:
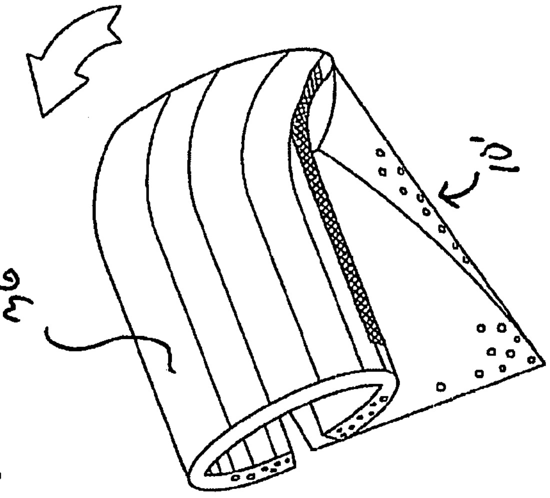
FIG. 14 shows a second step in folding the embodiment of FIG. 9A for collapsing the device.
Figure 13:
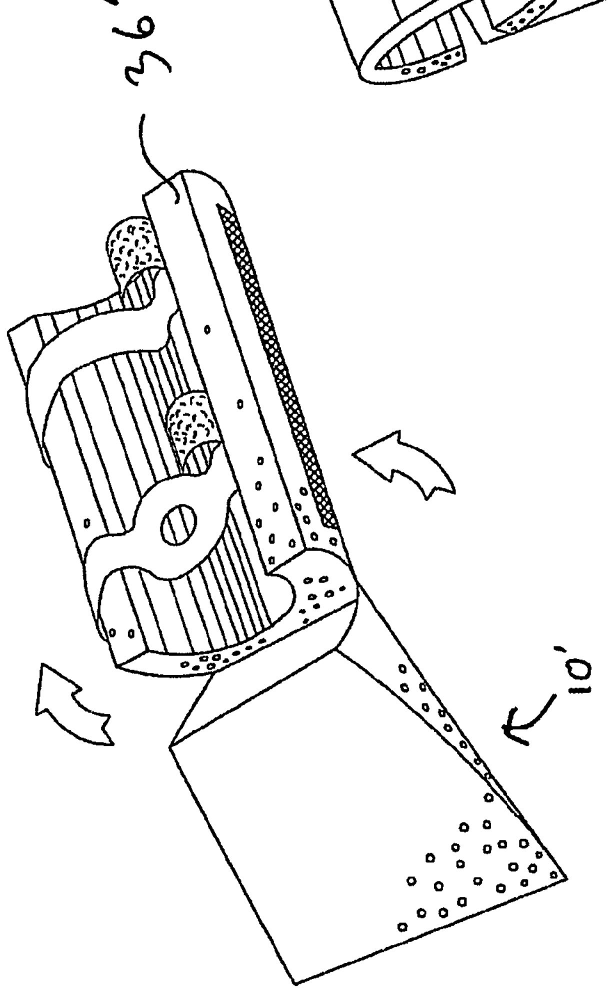
FIG. 13 shows a first step in folding the embodiment of FIG. 9A for collapsing the device.
Figure 15:
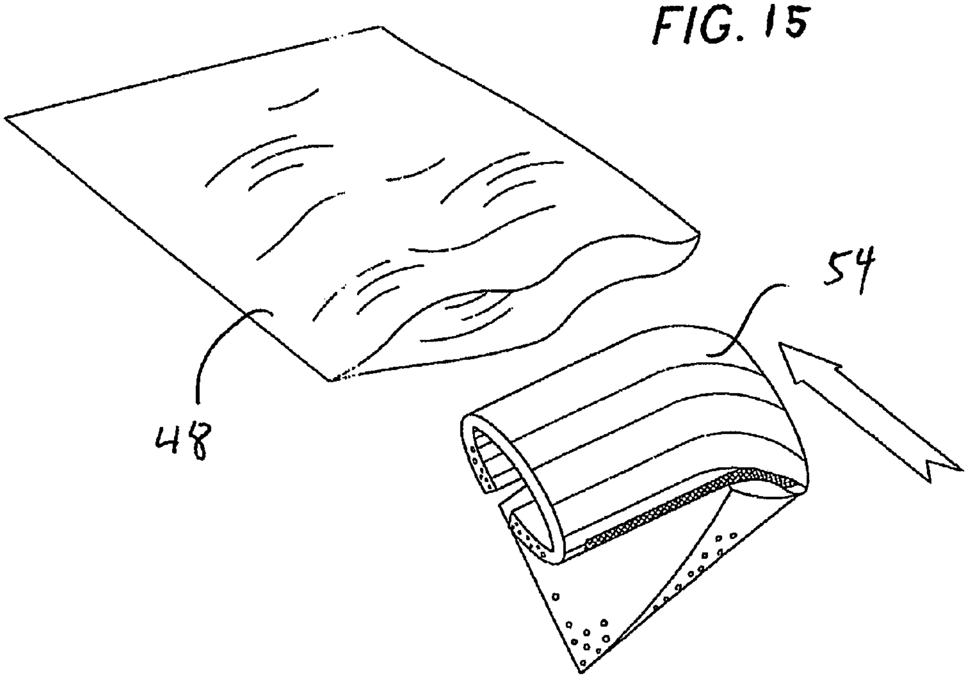
FIG. 15 shows the folded embodiment of FIG. 9A ready to be inserted into a plastic bag.
Figure 16:
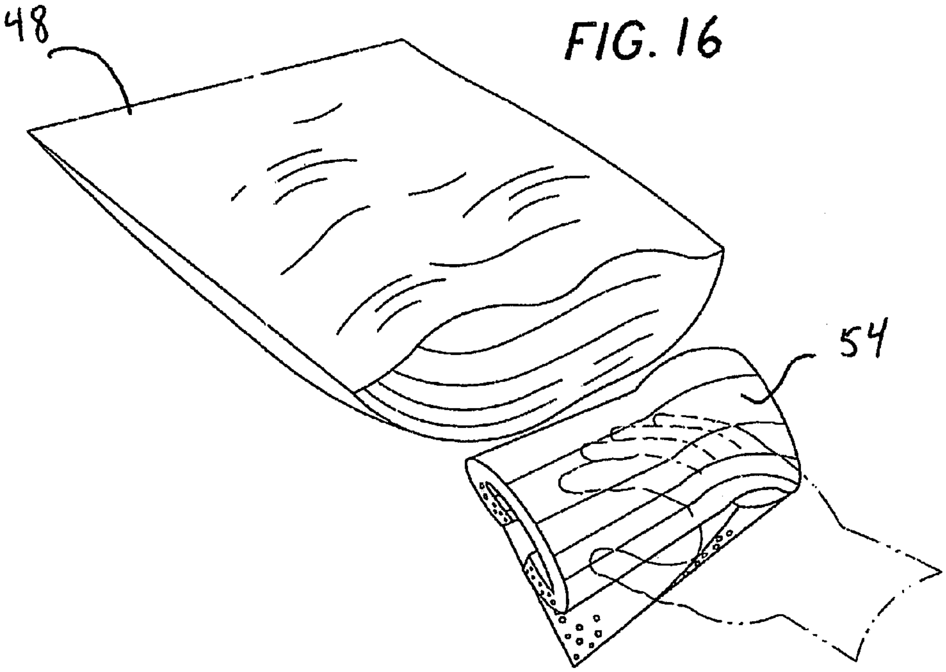
FIG. 16 shows the folded embodiment of FIG. 9A being inserted into a plastic bag.
Figure 19:
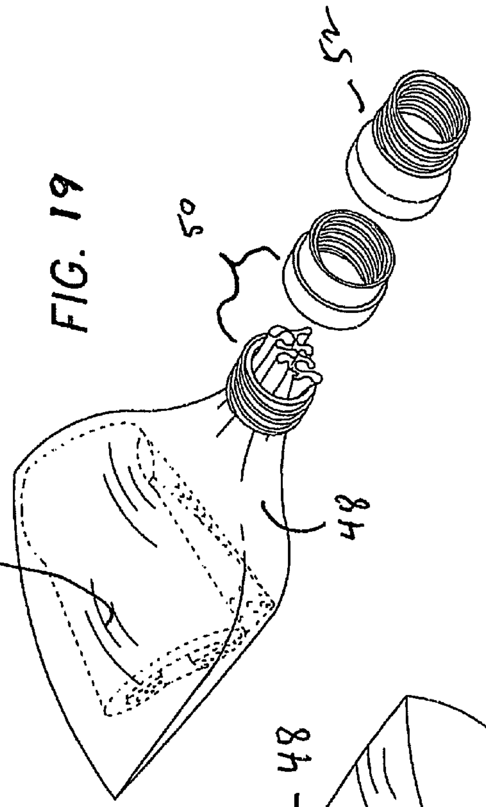
FIG. 19 shows the folded embodiment of FIG. 9A in a plastic bag with evacuation connectors ready to be attached.
Figure 17:
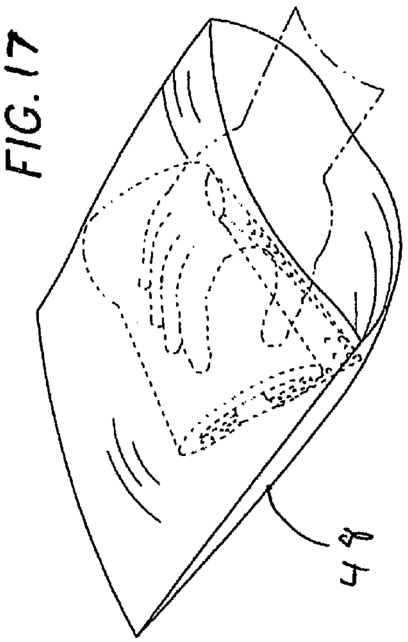
FIG. 17 shows the folded embodiment of FIG. 9A fully inserted into a plastic bag.
Figure 18:
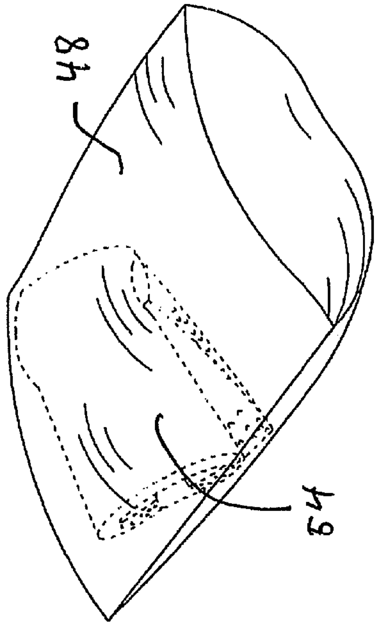
FIG. 18 shows the folded embodiment of FIG. 9A in a plastic bag.
Figure 21:
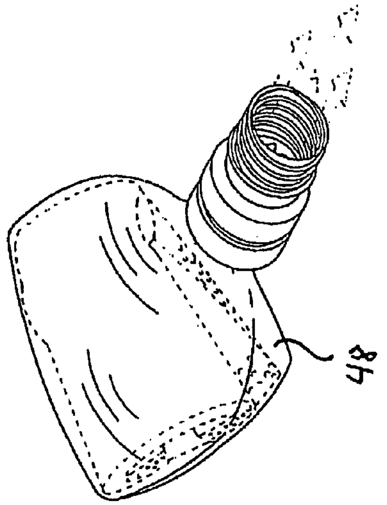
FIG. 21 shows the folded embodiment of FIG. 9A in a plastic bag with air being withdrawn.
Figure 22:
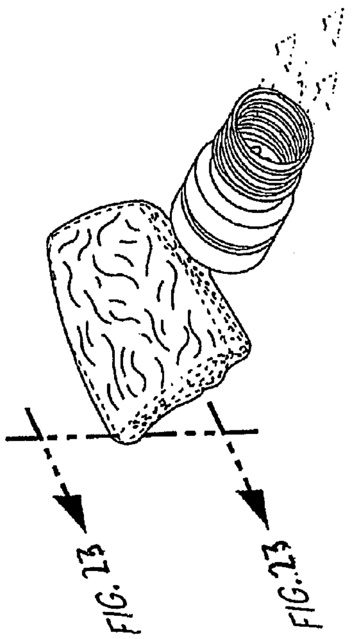
FIG. 22 shows the folded embodiment of FIG. 9A in a plastic bag in a collapsed configuration.
Figure 20:
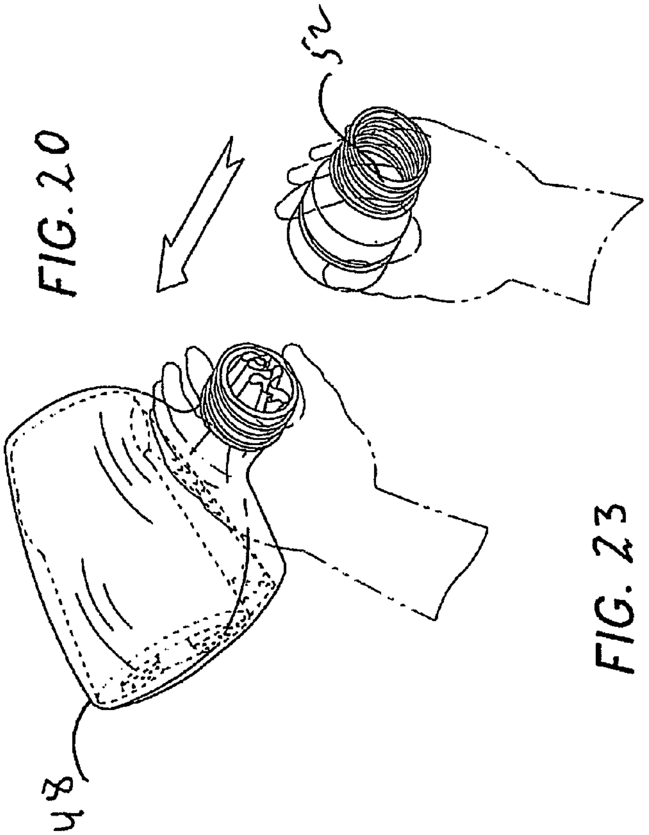
FIG. 20 shows the folded embodiment of FIG. 9A in a plastic bag with evacuation connectors being attached.
Figure 23:
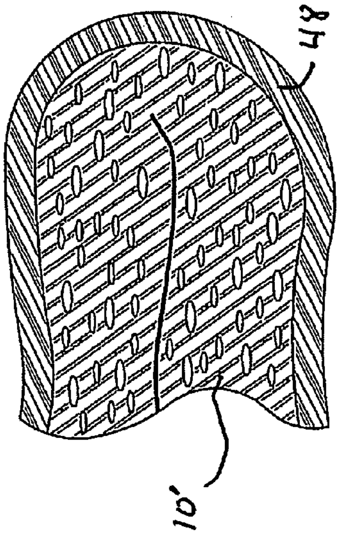
FIG. 23 is a diagrammatic cross-section along line 23-23 of FIG. 22 illustrating the collapsed nature of the cells of the plastic foam.
Figures 24, 25, 26A, 26B, 27:
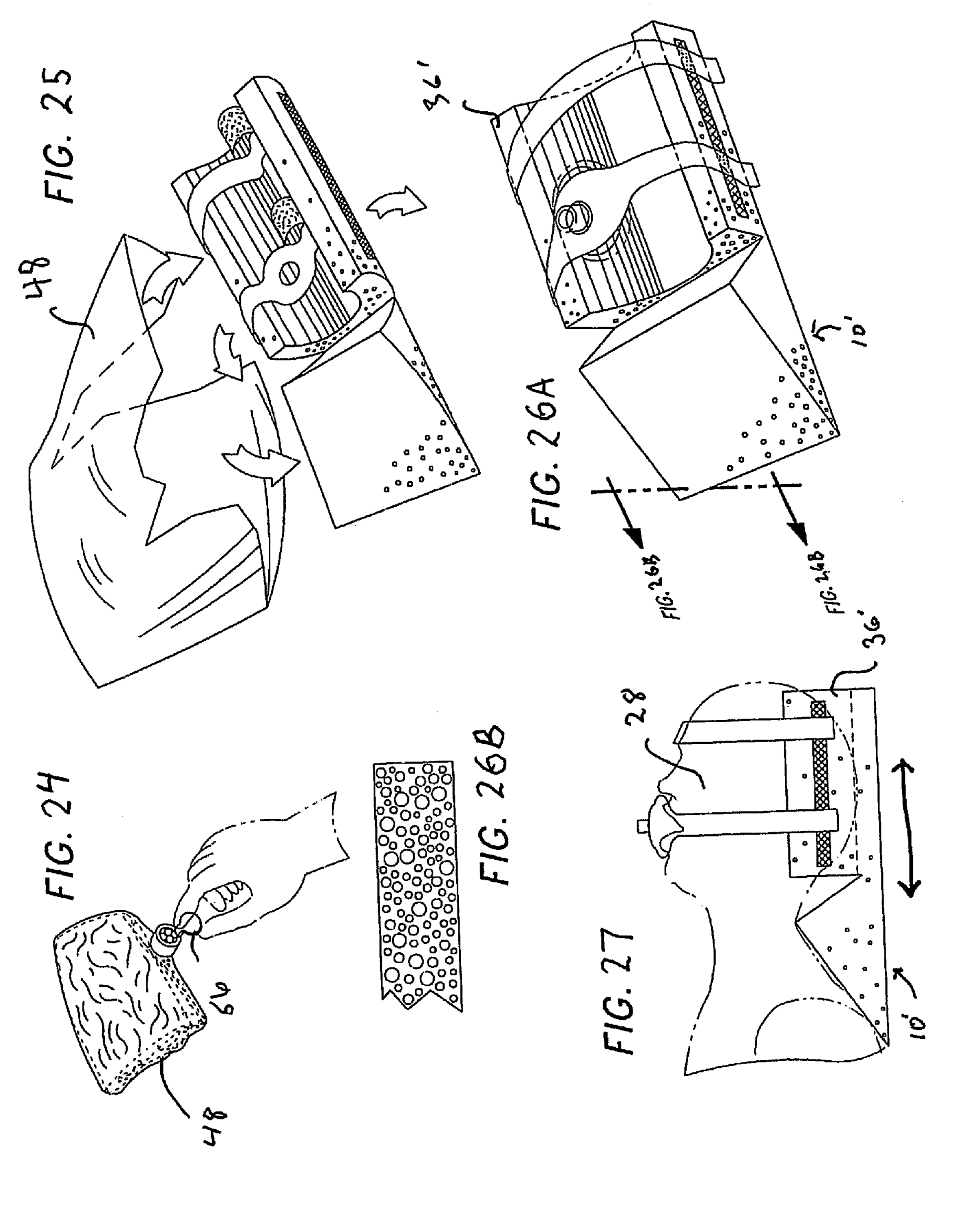
FIG. 24 shows the folded embodiment of FIG. 9A in a plastic bag completely collapsed being opened to allow reconstitution of the device.
FIG. 25 shows the reconstituted device being removed from the plastic bag and unfolded for use.
FIG. 26A shows the unfolded reconstituted embodiment of FIG. 9A which is essentially identical to the device of FIG. 13.
FIG. 26B shows a cross-section along line 26B-26B of FIG. 26A to illustrate that the cells of the foam have completely reinflated.
FIG. 27 shows a side view of the reconstituted device in relation to the head and neck of a patient.
Figure 28:
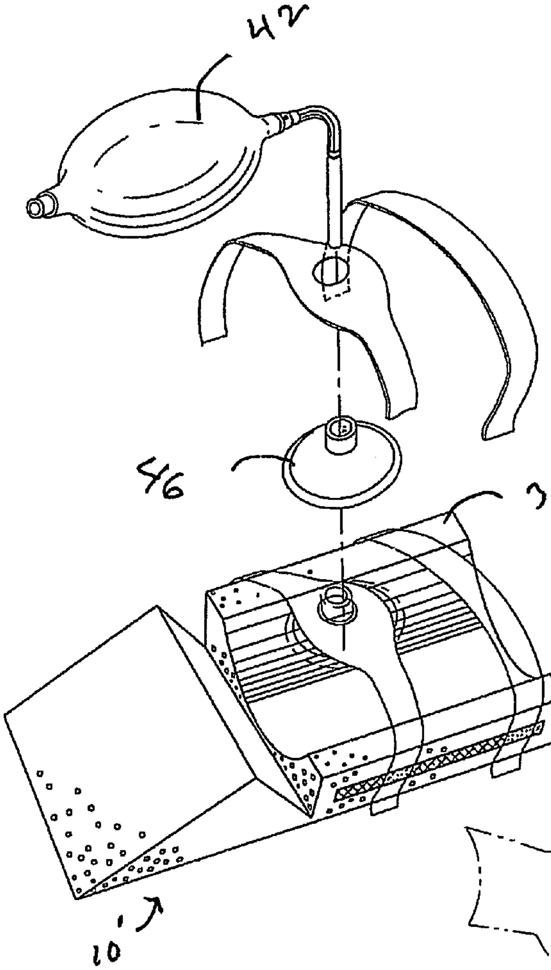
FIG. 28 shows the reconstituted device in relation to the straps and the resuscitator.
Figure 29:
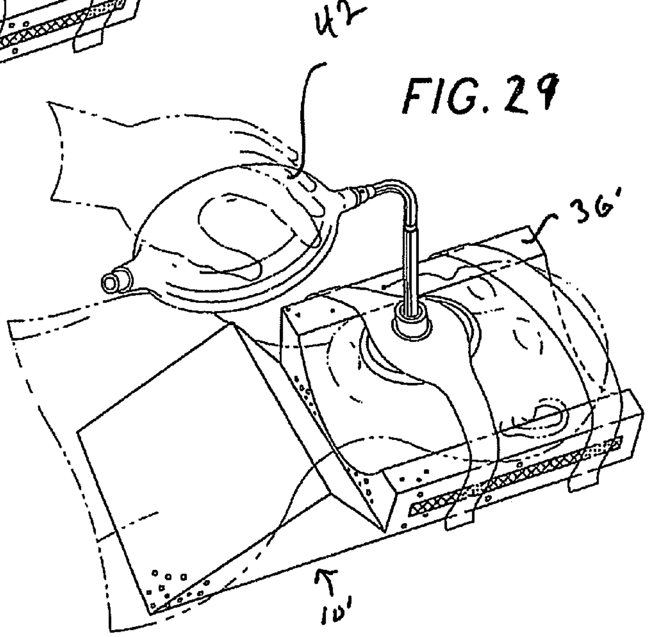
FIG. 29 shows a patient being resuscitated.

FIGS. 13 and 14 show the first two steps in the process of collapsing the foam embodiment of FIG. 9A. It will be apparent that this same process can be used on only the neck support 10' or on the head support wing 36' depending on the configuration of the finished device According to the process device is folded as indicated by the arrows in FIG. 13 to yield a more compacted device as shown in FIG. 14. Actual folded foam is somewhat more bulky but the bulkiness has been reduced in the figures to make it easier to appreciate the configuration involved. As shown in FIGS. 15 and 16 the folded device 54 is inserted into a plastic bag 48. The bag is advantageously made of a fairly heavy gauge plastic film such as the type often used to package sterile medical devices. After the folded device 54 is inserted into the bag 48, a connector 50 is attached to the bag (FIGS. 17-19). A hose 52 connected to a vacuum source is then connected (FIG. 22) and the bag 48 is evacuated (FIG. 24). As illustrated diagrammatically in FIG. 23, the evacuation process causes the open cell foam to collapse. Finally, the collapsed bag is sealed with an airtight disposable closure 56 to maintain the folded device 54 in a collapsed state. This process is merely illustrative. Those of skill in the art will readily extrapolate this to a production scale process.

As shown in FIG. 24 the collapsed device is used by opening the closure 56 whereupon the open cell foam re-expands returning the device to its original dimension. The expansion takes place within a minute or so. The device can be removed from the bag (FIG. 25) as expansion is going on. FIG. 26A shows that the device returned to its original state through the expansion of the open cell foam. This expansion is also illustrated in FIG. 26B which diagrammatically shows the cells of the foam returned to their original state. The re-expanded device is shown in use with a patient in FIG. 27. This should be compared to FIG. 8 showing the inflatable bladder embodiment of the device. The two headed arrow in FIG. 27 indicates that the entire device can be moved relative to the patient to obtain optimal pivoting of the patient's neck and the resulting opening of the patient's airway. Of course, the straps must be released to accomplish this movement relative to the patient.

It will also be appreciated that like most medical devices, the foam unit is preferably provided as a sterile item. The bag 48 (or similar flexible container) maintains sterility until the item is used. The device can be sterilized prior to being collapsed within the bag 48 (in which case the subsequent processing must occur under sterile clean room conditions. Alternatively, the foam device can be collapsed and packaged and the entire package then sterilized by heat or radiation as is well-known in the art.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. An emergency airway stabilizing device for use on a neck and head of a patient, comprising:

a contact region having a defined fulcrum acting as a support at a base of the patient's neck for applying an elevating pressure to the base of the patient's neck to allow the patient's neck to bend thereabout, while having a free portion of the patient's neck elevated but unsupported thereby facilitating tracheal access;

head support wings extending vertically on each side of the patient's head for stabilizing a position of the patient's head; and a connecting region for receiving the back of the patient's head at a level substantially lower than the fulcrum and for connecting the head support wings, wherein the contact region, the head support wings, and the connecting region are unitarily formed.

2. The airway stabilizing device according to claim 1, wherein the contact region is less than about three inches in length as measured along a length of a patient's neck.

3. The airway stabilizing device according to claim 1, wherein the device comprises collapsed open cell foam packaged under partial pressure, and further comprises means for inflating the device which means comprises ambient air under ambient pressure applied to the collapsed open cell foam when unpackaged.

4. The device of claim 1 where the fulcrum has a pyramidal shape and provides a defined line of support for the base of the patient's neck and falls away at a slope such that the free portion of the neck is unsupported.

5. The device of claim 1, wherein the head support wings are configured to be coupled to at least one strap for stabilizing the patient's head.

6. An emergency airway stabilizing device including a collapsed member, the collapsed member comprising:

a contact region sized and shaped for placement beneath the base of a patient's neck and configured to form a defined fulcrum to elevate the base of the patient's neck when the collapsed member is inflated; and head support wings unitarily formed with the contact region for stabilizing a position of the patient's head; and means for inflating the collapsed member thereby applying elevating force by means of the contact region, wherein the fulcrum allows the patient's neck to bend thereabout, while having a free portion of the patient's neck elevated but unsupported thereby facilitating tracheal access, and wherein the head support wings further include straps.

7. The device of claim 6, wherein the device is configured to be vacuum packaged in an airtight disposable closure in a collapsed state, and wherein the means for inflating the collapsed member comprises means for opening the closure thereby exposing the device to an ambient pressure.

8. An emergency airway stabilizing device for use on a neck and head of a patient and in contact with a back and sides of the patient's head and with a base of the patient's neck leaving a free portion of the patient's neck adjacent to the base of the patient's neck, comprising:

a contact region formed from resilient foam and sized and shaped for placement beneath the base of the patient's neck to elevate the base of the neck, the contact region forming a defined fulcrum and applying an elevating pressure to the base of the patient's neck to allow the patient's neck to bend thereabout, while having the free portion of the neck elevated but unsupported to facilitate tracheal access;

head support wings formed from resilient foam and extending vertically on each side of the patient's head for stabilizing a position of the patient's head when the base of the patient's neck is elevated by the fulcrum of the contact region; and a connecting region for receiving the back of the head at a level substantially lower than the fulcrum and for connecting the head support wings, wherein the contact region, the head support wings, and the connecting region are unitarily formed.

9. The device of claim 8 where the fulcrum has a pyramidal shape and provides a defined line of support for the base of the neck and falls away at a slope such that the free portion of the neck is unsupported.

10. The device of claim 8, wherein the device is configured to be vacuum packaged in an airtight disposable closure in a collapsed state.

11. The device of claim 8, wherein the head support wings are configured to be coupled to at least one strap for stabilizing the patient's head.

12. An emergency airway stabilizing device comprising:

a contact region formed from resilient foam and sized and shaped for placement beneath the base of a patient's neck and configured to form a defined fulcrum to elevate the base of the patient's neck; and head support wings unitarily formed with the contact region from resilient foam for stabilizing a position of the patient's head when the base of the patient's neck is elevated by the contact region, wherein the fulcrum allows the patient's neck to bend thereabout, while having a free portion of the patient's neck elevated but unsupported thereby facilitating tracheal access, and wherein the head support wings further comprises straps to immobilize the patient's head.

13. The device of claim 12, wherein the device is configured to be vacuum packaged in an airtight disposable closure in a collapsed state.

* * * * *